United States Patent [19]
Kesten

[11] Patent Number: 6,086,534
[45] Date of Patent: *Jul. 11, 2000

[54] APPARATUS AND METHOD OF MYOCARDIAL REVASCULARIZATION USING ULTRASONIC PULSE-ECHO DISTANCE RANGING

[75] Inventor: Randy J. Kesten, Mountain View, Calif.

[73] Assignee: Cardiogenesis Corporation, Sunnyvale, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/812,656

[22] Filed: Mar. 7, 1997

[51] Int. Cl.⁷ .................................................. A61B 17/36

[52] U.S. Cl. ............................................. 600/439; 606/15

[58] Field of Search ................................. 600/439, 462, 600/463, 450; 606/13, 15, 10, 7, 14, 16

[56] References Cited

U.S. PATENT DOCUMENTS

| | | | |
|---|---|---|---|
| 4,576,177 | 3/1986 | Webster, Jr. ......................... | 128/660 |
| 4,658,817 | 4/1987 | Hardy . | |
| 4,658,827 | 4/1987 | He et al. ............................... | 128/660 |
| 4,672,963 | 6/1987 | Barken ................................. | 128/303.1 |
| 4,802,487 | 2/1989 | Martin et al. ...................... | 128/662.06 |
| 4,936,281 | 6/1990 | Stasz .................................. | 128/660.03 |
| 4,958,327 | 9/1990 | Saitoh et al. ....................... | 367/7 |
| 5,109,830 | 5/1992 | Cho .................................... | 128/4 |
| 5,109,859 | 5/1992 | Jenkins . | |
| 5,158,085 | 10/1992 | Belikan et al. ................... | 128/660.03 |
| 5,196,006 | 3/1993 | Klopotek et al. . | |
| 5,242,386 | 9/1993 | Holzer . | |
| 5,243,988 | 9/1993 | Sieben et al. ..................... | 128/662.06 |
| 5,254,112 | 10/1993 | Sinofsky et al. . | |
| 5,313,950 | 5/1994 | Ishikawa et al. .................. | 128/662.06 |
| 5,323,781 | 6/1994 | Ideker et al. . | |

(List continued on next page.)

FOREIGN PATENT DOCUMENTS

| | | |
|---|---|---|
| 19537084 | 10/1995 | Germany . |
| 19606610 | 2/1998 | Germany . |
| WO 95/17131 | 6/1995 | WIPO . |
| 9635469 | 11/1996 | WIPO . |
| WO 97/25101 | 7/1997 | WIPO . |
| WO 98/17185 | 4/1998 | WIPO . |
| WO 98/30144 | 7/1998 | WIPO . |

OTHER PUBLICATIONS

Deckelbaum, "Cardiovascular Applications of Laser Technology", *Lasers in Surgery and Medicine*, 1994, 15:315–341.

*Primary Examiner*—George Manuel
*Assistant Examiner*—Shawna J Shaw
*Attorney, Agent, or Firm*—Heller Ehrman White & McAuliffe

[57] ABSTRACT

An apparatus and method of intraoperative myocardial revascularization of the myocardium of the heart of a patient. A catheter apparatus comprising an elongated catheter, an elongated laser wave guide slidably disposed within a lumen of the catheter, and an ultrasonic transducer secured to the distal end of the elongated laser wave guide, is inserted into the patient. The distal end of the lasing apparatus is guided to the portion of the patient's heart wall in which channels will be formed, and the ultrasonic transducer is activated to create brief pulses of ultrasonic energy. The transducer receives a returned ultrasonic echo from the heart wall. The ultrasonic echo is processed by signal processing elements. The processed ultrasonic echoes are displayed to show the distance between the epicardial and endocardial surfaces of the portion of the heart wall in which the revascularization energy is to be discharged, and the distance between the operative distal end of the myocardial revascularization device and such endocardial and epicardial surfaces. After distance measurements have been performed, channels are formed in the heart wall.

19 Claims, 3 Drawing Sheets

U.S. PATENT DOCUMENTS

| | | | |
|---|---|---|---|
| 5,337,682 | 1/1995 | Ueno et al. | 128/660.1 |
| 5,345,940 | 9/1994 | Seward et al. . | |
| 5,350,377 | 9/1994 | Winston et al. | 606/15 |
| 5,379,772 | 1/1995 | Imran | 128/662.06 |
| 5,380,316 | 1/1995 | Aita et al. | 606/7 |
| 5,389,096 | 2/1995 | Aita et al. . | |
| 5,409,000 | 4/1995 | Imran | 128/642 |
| 5,445,155 | 8/1995 | Sieben | 128/660.07 |
| 5,533,957 | 7/1996 | Aldea . | |
| 5,544,656 | 8/1996 | Pitsillides et al. | 128/661.04 |
| 5,601,084 | 2/1997 | Huaichuan et al. . | |
| 5,607,421 | 3/1997 | Jeevanandam et al. . | |
| 5,662,124 | 9/1997 | Wilk | 128/898 |
| 5,703,985 | 12/1997 | Owyang . | |
| 5,713,363 | 2/1998 | Seward et al. | 128/662.06 |
| 5,713,894 | 2/1998 | Murphy-Chutorian et al. . | |
| 5,724,975 | 3/1998 | Negus et al. . | |
| 5,730,741 | 3/1998 | Horzewski et al. . | |
| 5,755,714 | 5/1998 | Murphy-Chutorian . | |
| 5,766,163 | 6/1998 | Mueller et al. . | |
| 5,769,843 | 6/1998 | Abela et al. . | |
| 5,824,005 | 10/1998 | Motamedi et al. . | |
| 5,827,203 | 10/1998 | Nita . | |
| 5,853,368 | 12/1998 | Solomon et al. . | |
| 5,855,577 | 1/1999 | Muphy-Chutorian et al. . | |
| 5,891,133 | 4/2000 | Murphy-Chutorian | 606/7 |
| 5,893,848 | 4/1999 | Negus et al. . | |
| 5,997,531 | 12/1999 | Loeb et al. | 606/13 |
| 6,036,677 | 3/2000 | Javier, Jr. et al. | 604/264 |
| 6,039,727 | 3/2000 | Javier, Jr. et al. | 606/10 |
| 6,042,581 | 3/2000 | Ryan et al. | 606/45 |
| 6,053,911 | 4/2000 | Ryan et al. | 606/33 |

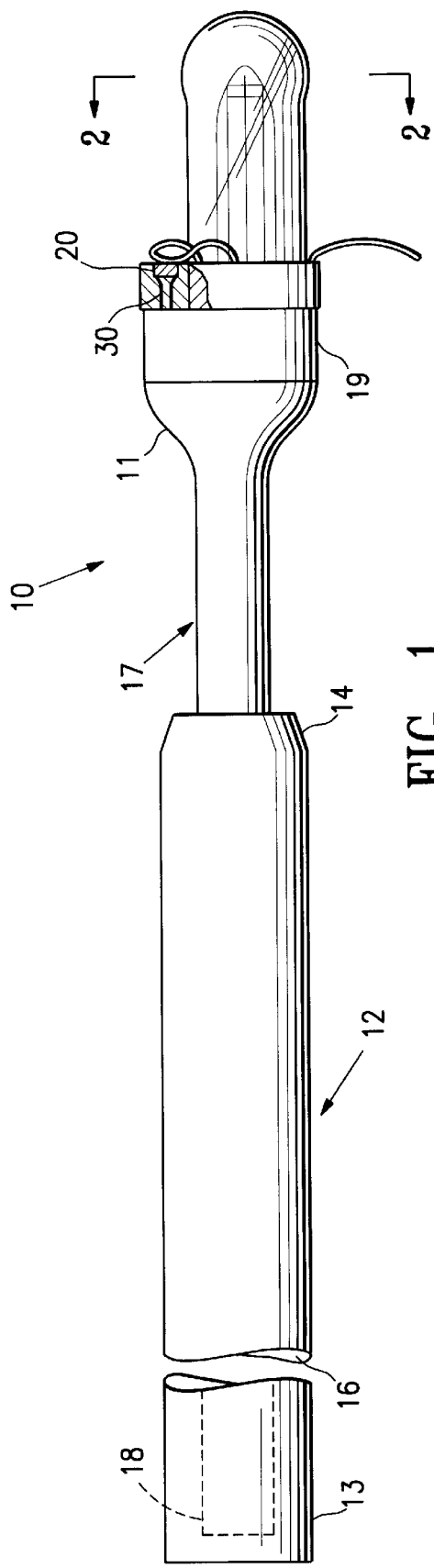
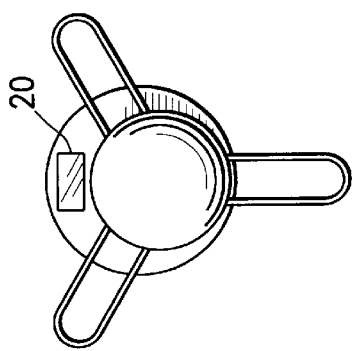

APPARATUS AND METHOD OF MYOCARDIAL REVASCULARIZATION USING ULTRASONIC PULSE-ECHO DISTANCE RANGING

BACKGROUND OF THE INVENTION

The invention relates to the field of medical devices, and more particularly to an apparatus and method for measuring the distance between the operative distal end of a myocardial revascularization device and the endocardial and epicardial surfaces of the heart wall of a patient.

In the treatment of cardiovascular disease, transmyocardial revascularization (TMR) is a well known technique in which channels are formed in a patient's heart wall to supply blood flow to the ischemic heart tissue and to treat angina. The channels extend through the heart wall muscular surface, or myocardium, located between the epicardium and endocardium of the heart wall. In laser transmyocardial revascularization (LMR), a laser is used to form one or more channels in a patient's heart wall defining the heart chamber. The laser energy is typically transmitted from the laser to the heart tissue by an optical fiber, with a lens on the distal end of the optical fiber operatively engaging the heart tissue to be revascularized. Other energy systems, such as electrodes, may be used for myocardial revascularization.

Initial revascularization procedures required the chest wall to be opened for insertion of the revascularization device and penetration of the entire heart wall to form a channel through the myocardium into the endocardium. Copending application, Ser. No. 08/368,409, filed on Dec. 30, 1994 which is incorporated herein in its entirety, describes an intravascular system for percutaneous transmyocardial revascularization (PTMR) which eliminates the need of the prior procedures for opening the chest cavity and penetrating the entire heart wall. The PTMR system is introduced into a peripheral artery and advanced through the patient's arterial system into the left ventricle of the patient's heart, from where the revascularization channels are formed through the endocardium and into the myocardium.

Transmyocardial revascularization requires accurate measurement of the thickness of the patient's heart wall, in order for the procedure to be performed with maximum safety and effectiveness. Establishing the thickness of the heart wall at the location where TMR energy is to be discharged decreases the likelihood of injury to the patient from transmural perforation, and allows the physician to precisely control the channel formation by controlling of the depth of penetration of the discharged energy. TMR also requires establishing the distance between the operative distal end of a TMR device and the heart wall surface to determine when activation of the TMR device will effectively form channels within the patient's heart wall. Intimate contact between the operative distal end of the TMR device and the patient's heart tissue is necessary to provide sufficient transmission of the channel forming energy to the heart wall. Ranging information regarding the TMR device is therefore necessary to determine when contact between the TMR device and the heart wall surface has been achieved.

One of the difficulties with currently used PTMR devices has been the inability to accurate measurement of the thickness of the patient's heart wall at the precise location where TMR channels are to be formed. Information regarding wall thickness is currently obtained through echocardiographic analysis that may be performed either before or during the TMR procedure. However, methods of measuring heart wall thickness, such as transthoracic or transesophogeal echocardiography, only provide information for a small sample of locations on the heart wall and do not provide information regarding the precise location in which the TMR channels are to be formed.

Current methods used in TMR for determining contact with the heart wall have proven inadequate. In typical TMR devises, the physician determines the point at which the operative distal end has contacted the endocardium by observation of a fluoroscopic image of the optical assembly. However, fluoroscopic imaging requires a substantial amount of fluoroscopy time, and therefore exposes the patient to a large amount of radiation. Alternatively, the physician may infer contact from the observation of ectopic beats on the electrocardiogram, or from the observation of a reciprocating motion in the PTMR device produced when the device is in contact with the endocardial surface. However, these methods increase the expertise required to perform the procedure, and often provide ambiguous information.

What has been needed is the ability to reliably measure the thickness of the heart wall to be revascularized, and the distance between the operative distal tip of a PTMR device and the heart wall surface, in order to precisely control the channels formed in the patient's heart wall during PTMR. The invention satisfies these and other needs.

SUMMARY OF THE INVENTION

The invention is directed to an apparatus and method of transmyocardial revascularization utilizing pulsed echo ultrasonic ranging. Specifically, the ultrasonic ranging provides information on the thickness of the heart wall in the precise location in which the revascularization energy is to be discharged, and the distance separating the operative distal end of the revascularization device from the heart wall.

The catheter apparatus of the invention generally has an elongated laser wave guide with an ultrasonic transducer on a distal end of the wave guide. The catheter apparatus also includes an elongated catheter having proximal and distal ends and a lumen therein which slidably receives the elongated laser wave guide.

The present invention comprises a method of intraoperative myocardial revascularization of the myocardium of the heart of a patient. A catheter apparatus comprising an elongated catheter, an elongated laser wave guide slidably disposed within a lumen of the catheter, and an ultrasonic transducer secured to the distal end of the elongated laser wave guide, is inserted into the patient. The distal end of the lasing apparatus is guided to the portion of the patient's heart wall in which channels will be formed, and the ultrasonic transducer is activated to create brief pulses of ultrasonic energy. The transducer receives a returned ultrasonic echo from the heart wall. The ultrasonic echo is used to measure the distances between the distal end of the elongated laser wave guide and the endocardial and epicardial surfaces of the desired portion of the wall of the patient's heart. After distance measurements have been performed, channels are formed in the heart wall. The distal end of the laser wave guide is maintained against the desired portion of the heart wall while transmitting laser energy from a remote laser source through the laser wave guide and out the distal end thereof in a beam onto the heart wall with sufficient energy and for a sufficient time to form a channel through the wall of the patient's heart.

When the ultrasonic transducer is activated to create brief pulses of ultrasonic energy, an echo of the pulses from the heart wall returns to the transducer. The transducer receives a first returned ultrasonic echo from the surface of the heart wall closest to the transducer, and a second returned ultrasonic echo from the furthermost surface of the heart wall. For example, in PTMR when the TMR device is within a chamber of the patient's heart, the distal end of the TMR device is positioned directly adjacent to the endocardial surface which lines the inside of the heart chamber. Because the endocardial surface is the heart wall surface closest to the ultrasonic transducer, the first returned ultrasonic echo is from the endocardial surface. A second ultrasonic echo is returned from the epicardial surface on the outer side of the heart wall furthermost from the distal end of the TMR device. Therefore, the position of the distal end of the TMR device relative to the endocardial surface is indicated by the first ultrasonic echo, and the position relative to the epicardial surface is indicated by the second ultrasonic echo.

In accordance with the invention, the ultrasonic transducer is used to measure the distances between the distal end of the elongated laser wave guide and the endocardial and epicardial surfaces of the portion of the wall of the patient's heart in which the revascularization energy is to be discharged. Measurement of such distances allows for a determination of the thickness of the heart wall to be revascularized, and whether the operative distal tip of a PTMR device is in contact with the heart wall surface.

The ultrasonic echo is processed by signal processing elements. The processed ultrasonic echoes are displayed to show the distance between the epicardial and endocardial surfaces of the portion of the heart wall in which the revascularization energy is to be discharged, and the distance between the operative distal end of the myocardial revascularization device and such endocardial and epicardial surfaces.

The apparatus and method of the invention provides for improved transmyocardial revascularization by allowing more precise control over the channel formation. Measurement and display of the distances between the operative distal end of the TMR device and the endocardial and epicardial surfaces greatly reduces the risk of transmural perforation. Moreover, because the thickness of the heart wall is known, the physician is able to control the channel formation by selecting the depth of penetration of the lasing energy. Additionally, because the position of the distal end of the TMR device relative to the heart wall is known, the premature discharge of lasing energy before the operative distal end of the TMR device has contacted the heart wall is eliminated. These and other advantages of the invention will become more apparent from the following detailed description of the invention and the accompanying exemplary drawings.

BRIEF DESCRIPTION OF THE DRAWINGS

FIG. 1 is an enlarged longitudinal cross sectional view of a catheter apparatus which embodies features of the invention.

FIG. 2 is a transverse cross sectional view of the catheter apparatus shown in FIG. 1 taken along the lines 2—2.

DETAILED DESCRIPTION OF THE INVENTION

Figure 3:
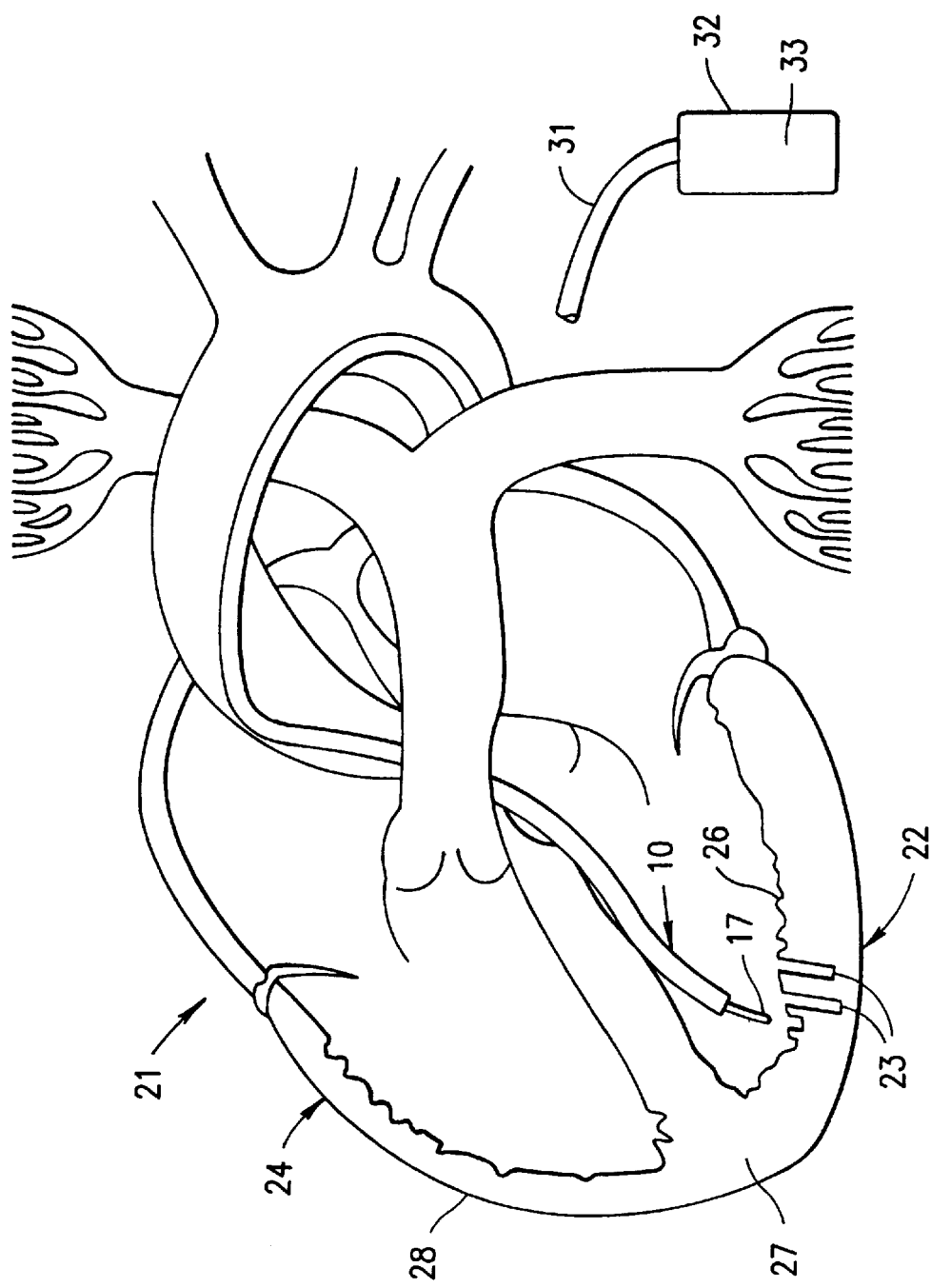
FIG. 3 is a longitudinal cross sectional view of a human heart with a transmyocardial revascularization catheter apparatus therein.

As shown in FIG. 1, the catheter apparatus 10 of the invention suitable for performing myocardial revascularization on a desired portion of a wall of the patient's heart generally includes a distal end 11, an elongated catheter 12 having proximal 13 and distal 14 ends and a lumen 16 therein, and an elongated laser wave guide 17 having proximal 18 and distal 19 ends and being slidably disposed within the lumen of the elongated catheter 11. An ultrasonic transducer 20 secured to the distal end 19 of the elongated laser wave guide 17 emits bursts of ultrasonic energy. In the embodiment illustrated in FIG. 1, the ultrasonic transducer 20 is mounted on a side of the laser wave guide 17. FIG. 2 illustrates a cross section of the catheter apparatus shown in FIG. 1, taken along lines 2—2.

An apparatus suitable for implementing the method of myocardial revascularization of the present invention is embodied in the apparatus illustrated in FIG. 1. FIG. 3 illustrates a TMR device positioned within a heart chamber. Referring to FIGS. 1 and 3, the method of the present invention comprises providing a catheter apparatus 10 suitable for performing myocardial revascularization. As illustrated in FIG. 3, the patient's heart 21 includes a portion 22 at which a myocardial revascularization channel 23 is to be formed in the wall 24 of the heart, said wall comprising an endocardial surface 26, a myocardium 27, and an epicardial surface 28. The distal end 11 of the apparatus 10 is guided within the patient to the desired portion 22 of the heart wall 24 through which a channel 23 is to be formed. The ultrasonic transducer is then activated to create a pulse of ultrasonic energy. An ultrasonic echo retrieved by the ultrasonic transducer is monitored to measure distances between the distal end 19 of the elongated laser wave guide 17 and the endocardial 26 and epicardial 28 surfaces of the desired portion 22 of the wall 24 of the patient's heart 21.

In one aspect of the invention, fine wire leads 30 operably connect the ultrasonic transducer 20 to signal processing elements 32 located externally to the laser wave guide 17. The fine wire leads 30 may be contained within the lumen 16 of the elongated catheter or within a catheter wall defining the lumen 16. The fine wire leads 30 connect to a suitable cable 31 on the proximal end of the catheter 12 which connects to the signal processing elements 32 and a display console 33. The signal processing elements 32 process the ultrasonic echo for display of distances measured thereby. The signal processing elements 32 generate and amplify an ultrasonic pulse emitted from the ultrasonic transducer 20, and amplify and process for display the echo signal received by the transducer 20. Typical pulse echo techniques are used to create a clock driven pulse generator and to demodulate and amplify the returned echo signal.

Figure 4:
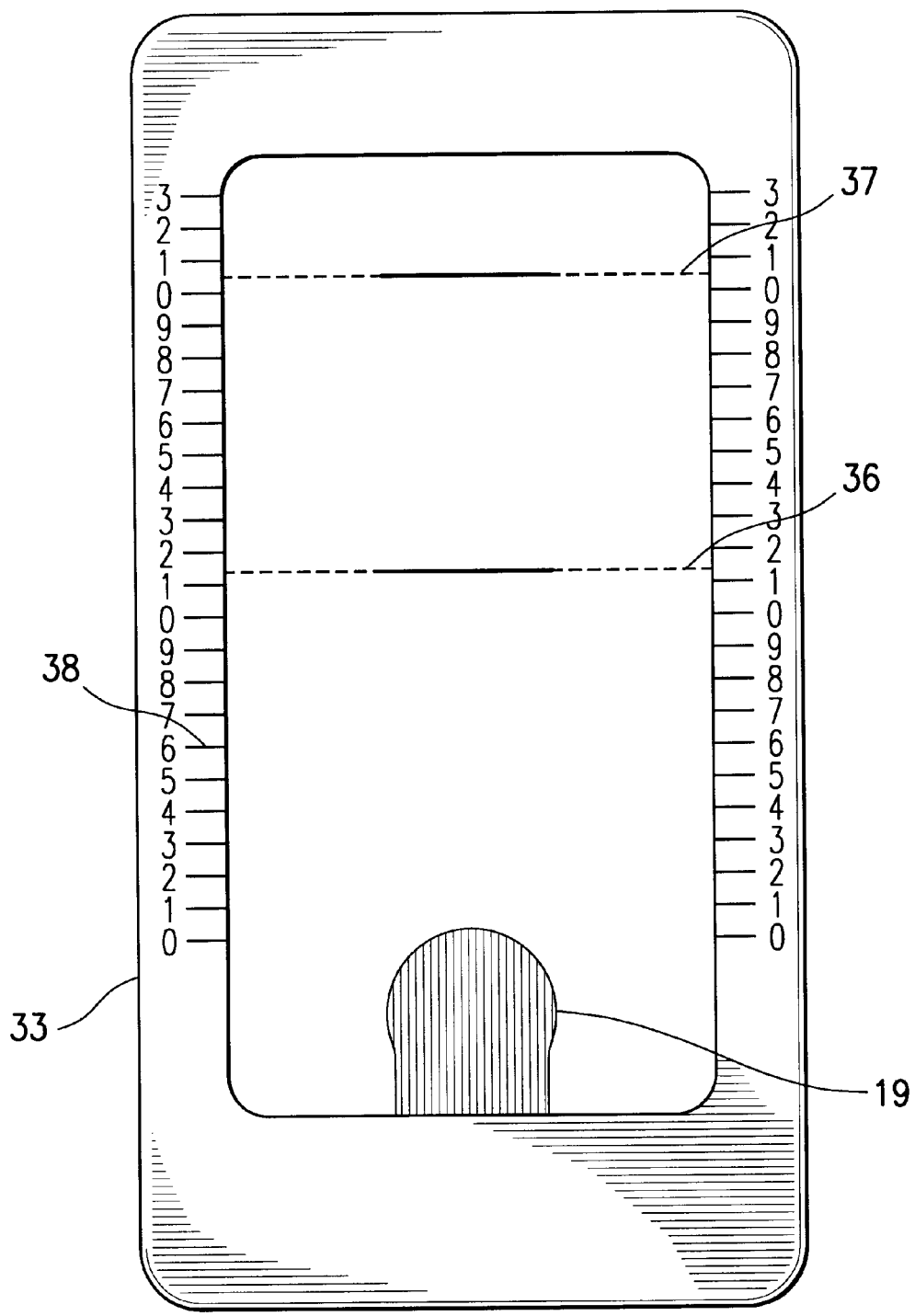
FIG. 4 is illustrates a display console which embodies features of the invention.

FIG. 4 illustrates a display console 33 for displaying the processes echo signal. The display console 33 indicates the distance between the distal end 19 of the laser wave guide 17 and the endocardial surface 26, as well as the thickness of the myocardium 27 directly in front of the laser wave guide distal end 19. The display console 33 may be a cathode ray tube (CRT) monitor, a liquid crystal display (LCD) screen, or other similar suitable devices. In the embodiment illustrated in FIG. 4, the display console 33 has a permanently imprinted representation of the distal end 19 of the laser wave guide 17. Displayed on the console are two dashed lines; the lower line 36 represents the location of the endocardial surface as determined by the initial echo of the ultrasonic pulse during a PTMR procedure, and the upper line 37 represents the location of the epicardial surface 28 as determined by the second echo. A scale 38 is shown on the display console 33 to provide distance measurements. However, other suitable display systems exist, including a linear series of light emitting diodes (LEDs) or LCD segments displaying the positions of the endocardial 26 and epicardial 28 surfaces relative to the laser wave guide 17 distal end 19 (not shown).

In one aspect of the invention, the frequency of the ultrasonic transducer 20 is selected to provide a desired depth of penetration into the wall 24 of the patient's heart 21. In one embodiment, the frequency of the ultrasonic transducer 20 is about 2 to about 9 MHz. The catheter apparatus 10 components are chosen so that the desired frequency coincides with the resonant frequency of the ultrasonic transducer 20.

In a presently preferred embodiment, the ultrasonic transducer 20 is a piezoelectric crystal, such as lead zirconium titanate (PZT) transducers. However, one skilled in the art will recognize that many suitable transducers exists. In the embodiment illustrated in FIGS. 1 and 2, the ultrasonic transducer 20 is a rectangular shape. However, alternatively shaped transducers are also suitable, including an annular transducer positioned coaxially around the distal end 19 of the laser wave guide 17 (not shown). Mechanical mounting of the transducer is performed in such a way as to provide moderate acoustic damping behind the ultrasonic transducer 20 and efficient acoustic coupling in front of the transducer. The ultrasonic transducer 20 may be mounted on the laser wave guide 17 using suitable materials, such a conductive epoxies (not shown), and coatings (not shown), such as polystyrene, may be applied to the transducer 20.

While the present invention has been described herein in terms of certain preferred embodiments, modifications and improvements may be made to the invention without departing from the scope thereof.

What is claimed is:

1. A catheter apparatus suitable for performing myocardial revascularization on a desired portion of a wall of a patient's heart, comprising:
   a) an elongated catheter having proximal and distal ends and a lumen therein;
   b) an elongated laser wave guide having a proximal end and a distal end slidably disposed within the lumen of the elongated catheter and configured to extend beyond the distal end of the elongated catheter; and
   c) an ultrasonic transducer which is secured to the distal end of the elongated laser wave guide and which is configured to emit ultrasonic energy substantially parallel to a longitudinal axis of the elongated laser wave guide and to receive ultrasonic echoes substantially parallel to a longitudinal axis of the elongated laser wave guide to facilitate determining distances between an energy emitting surface of the distal end of the elongated laser wave guide and surfaces of the desired portion of the wall of the patient's heart.

2. The catheter apparatus of claim 1 wherein the ultrasonic transducer is a piezoelectric crystal.

3. The catheter apparatus of claim 1 wherein an electrical conductor operably attached to the ultrasonic transducer connects the ultrasonic transducer to an external signal processor.

4. The catheter apparatus of claim 1 wherein the ultrasonic transducer operates at a frequency of about 2 to about 9 MHz.

5. A method of forming a channel in a desired portion of a wall of a patient's heart, comprising:
   a) providing a catheter apparatus having a distal end, comprising an elongated catheter having proximal and distal ends and a lumen therein; an elongated laser wave guide having proximal and distal ends slidably disposed within the lumen of the elongated catheter and configured to extend beyond the distal end of the elongated catheter; and an ultrasonic transducer which is secured to the distal end of the elongated laser wave guide and which is configured to emit ultrasonic energy substantially parallel to a longitudinal axis of the elongated laser wave guide and to receive ultrasonic echoes substantially parallel to a longitudinal axis of the elongated laser wave guide to facilitate determining distances between an energy emitting surface of the distal end of the elongated laser wave guide and surfaces of the desired portion of the wall of the patient's heart;
   b) guiding the distal end of the catheter apparatus within the patient to the desired portion of the patient's heart wall into which a channel is to be formed;
   c) activating the ultrasonic transducer to create pulses of ultrasonic energy directed to a desired portion of the patient's heart wall;
   d) receiving ultrasonic echo pulses reflected from surfaces of the patient's heart wall by the ultrasonic transducer;
   e) monitoring the ultrasonic echo pulses to determine the distances between an energy emitting surface of the distal end of the elongated laser wave guide and surfaces of the desired portion of the wall of the patient's heart; and
   f) maintaining the distal end of the laser wave guide against the desired portion of the heart wall while transmitting laser energy from a remote laser source through the laser wave guide and out the distal end thereof in a beam onto the heart wall with sufficient energy and for a sufficient time to form a channel into the wall of the patient's heart.

6. The method of claim 5 further including processing the ultrasonic echo using signal processing elements operably connected to the ultrasonic transducer.

7. The method of claim 6 further including displaying the ultrasonic echo to show the distance between the epicardial and endocardial surfaces of the portion of the heart wall, and the distance between the distal end of the elongated laser wave guide and such endocardial and epicardial surfaces.

8. The method of claim 5 wherein a frequency of the ultrasonic transducer is selected to provide a desired depth of penetration into the wall of the patient's heart.

9. The method of claim 5 wherein the frequency of the ultrasonic transducer is about 2 to about 9 MHz.

10. A method of determining a distance between a distal end of an intravascular apparatus suitable for performing myocardial revascularization and of a portion of a patient's heart wall on which myocardial revascularization is to be performed, comprising creating pulses of ultrasonic energy from an ultrasonic transducer which is secured to a distal end of an elongated laser waveguide disposed within a lumen of the apparatus and which has an emitting surface essentially perpendicular to a longitudinal axis of the intravascular apparatus, receiving ultrasonic echo pulses reflected from surfaces of the heart wall, determining from the ultrasonic echo pulses the distance between an energy emitting surface of the distal end of the elongated laser wave guide and surfaces of the portion of the heart wall and displaying the distance between the energy emitting surface of the distal end of the elongated laser wave guide and the surfaces of the portion of the heart wall on a console.

11. The method of claim 10 wherein a frequency of the ultrasonic transducer is selected to provide a desired depth of penetration into the wall of the patient's heart.

12. The method of claim 10 wherein the frequency of the ultrasonic transducer is about 2 to about 9 MHz.

13. The method of claim 10 further including processing the ultrasonic echoes using signal processing elements operably connected to the ultrasonic transducer.

14. The method of claim 10 further including displaying the ultrasonic echo pulses to show the distance between surfaces of the portion of the heart wall, and the distance between the distal end of the intravascular apparatus and such surfaces.

15. A method of forming a channel in a desired portion of a wall of a patient's heart, comprising:
   a) providing an intravascular apparatus having an elongated laser wave guide having proximal and distal ends; and an ultrasonic transducer which is secured to the distal end of the elongated laser wave guide and which is configured to emit ultrasonic energy substantially parallel to a longitudinal axis of the elongated laser wave guide and to receive ultrasonic echoes substantially parallel to a longitudinal axis of the elongated laser wave guide to facilitate determining distances between an energy emitting surface of the distinct end of the elongated laser wave guide and surfaces of the desired protion of the wall of the patients's heart;
   b) guiding the distal end of the intravascular apparatus within the patient to the desired poriton of the patient's heart wall into which a channel is to be formed;
   c) activating the ultrasonic transducer to create pulses of ultrasonic energy directed to a desired portion of the patient's heart wall;
   d) receiving ultrasonic echo pulses reflected from surfaces of the patients's heart wall by the ultrasonic transducer;
   e) monitoring the ultrasonic echo pulses with a signal processing element and displaying a distance between an energy emitting surface of the distal end of the elongated laser wave guide and the surface of the desired portion of the wall of the patient's heart on a display console; and
   f) maintaining the distal end of the laser wave guide against the desired portion of the heart wall while transmitting laser energy from a remote laser source through the laser wave guide and out the distal end thereof in a beam onto the heart wall with sufficient energy and for a sufficient time to form a channel into the wall of the patient's heart.

16. The method of claim 15 further including processing the ultrasonic echo using signal processing elements operably connected to the ultrasonic transducer.

17. The method of claim 15 further including displaying the ultrasonic echo pulses ot show the distance between surfaces of the portion of the heart wall, and the distance between the distal end of the intravascular apparatus and such surfaces.

18. The method of claim 15 wherein a frequency of the ultrasonic transducer is selected to provide a desired depth of penetration into the wall of the patients's heart.

19. The method of claim 15 wherein the frequency of the ultrasonic transducer is about 2 to about 9 MHz.

* * * * *